(12) United States Patent
Proctor

(10) Patent No.: US 7,286,635 B2
(45) Date of Patent: *Oct. 23, 2007

(54) ELEMENTAL ANALYZER APPARATUS AND METHOD

(76) Inventor: Raymond J. Proctor, 7125 Lipmann St., San Diego, CA (US) 92122

( * ) Notice: Subject to any disclaimer, the term of this patent is extended or adjusted under 35 U.S.C. 154(b) by 108 days.

This patent is subject to a terminal disclaimer.

(21) Appl. No.: 11/305,463

(22) Filed: Dec. 16, 2005

(65) Prior Publication Data

US 2006/0093087 A1 May 4, 2006

Related U.S. Application Data

(63) Continuation-in-part of application No. 10/754,972, filed on Jan. 10, 2004, now Pat. No. 7,027,555.

(60) Provisional application No. 60/440,041, filed on Jan. 15, 2003.

(51) Int. Cl.
*G01N 23/04* (2006.01)

(52) U.S. Cl. ............... 378/57; 378/119; 250/358.1; 376/156

(58) Field of Classification Search ............ 378/57, 378/120, 119; 250/358.1, 359.1, 360.1; 376/156–159
See application file for complete search history.

(56) References Cited

U.S. PATENT DOCUMENTS

| | | |
|---|---|---|
| 5,115,459 A | 5/1992 | Bertozzi |
| 5,420,905 A | 5/1995 | Bertozzi |
| 5,784,430 A * | 7/1998 | Sredniawski ............ 378/57 |
| 6,973,158 B2 * | 12/2005 | Besson ................ 378/16 |
| 7,027,555 B2 * | 4/2006 | Proctor ................ 378/57 |

OTHER PUBLICATIONS

R.J.Proctor, "On-Line Prompt Gamma Neutron Activation Analyzers", Process/Industrial Instruments Control Handbook, Fifth Edition, Gregory K. McMillan(Ed), 10.161, 1999.
H.Langhoff, "Resonance Fluorescence in Re-187", Phys. Rev., vol. 135, No. 1B, 1964.
Flywheel Product Sheet, Optimal Energy Systems, 2560 W.237th Street, Torrance, CA90505.
B.D.Sowerby, "A Comparison of Gamma-Ray Resonance Scattering Techniques for Borehole Analysis", Nucl. Instr. And Methods, 108, 317, 1973.
B.Arad, "Resonance Fluorescence of Excited Nuclear Levels in the Energy Range 5-11 MeV", Ann. Rev. Nucl. Sci., 24, 35, 1974.

* cited by examiner

*Primary Examiner*—Jurie Yun

(57) ABSTRACT

An elemental analyzer for identifying quantities of one or more elements in a material has a container for holding a material to be analyzed, a resonant gamma ray source unit for directing resonant gamma rays into the material in the container, and at least one detector for detecting gamma rays resonantly scattered by at least one predetermined element in the material. The resonant gamma ray source unit has an outer housing of gamma ray shield and a radiological shield material, with an inner chamber and an aperture directed towards the container, a moving gamma ray generator source of predetermined materials mounted in the chamber, the materials being selected from a predetermined group of materials which emit resonant gamma rays when exposed to particles or photons, the source being directed towards said aperture, and a source of particles or photons positioned in the chamber adjacent the gamma ray generator source.

30 Claims, 8 Drawing Sheets

ELEMENTAL ANALYZER APPARATUS AND METHOD

CROSS REFERENCE TO RELATED APPLICATIONS

This application is a Continuation In Part of application Ser. No. 10/754,972 filed Jan. 10, 2004, now U.S. Pat. No. 7,027,555, which claims the benefit of priority of U.S. provisional application Ser. No. 60/440,041 filed Jan. 15, 2003.

BACKGROUND OF THE INVENTION

The present invention relates to material elemental analysis, and is particularly concerned with a non-invasive analyzer apparatus and method for determining quantities of particular elements in large quantities of material.

The importance of elementally enriched matter is inestimable because of the products it makes possible . . . copper for wiring; iron ore, bauxite, platinum and many other ores for cars; phosphate, potash and sulfur for growing crops; gold for electronics and decoration; kaolin and titanium for paints; uranium, coal and oil for fuels; and even ferrous, non-ferrous and heavy metals from recycled waste materials. The Special Nuclear Materials like Thorium, Uranium and Plutonium whether contained in mineral ores or purified and buried within commercial materials are also of critical interest to society. Historically in the winning of useful elements from the earth or recycled material streams, physical sub-samples were collected and analyzed in a laboratory for the quantity and quality of the elements that they contained. The methods were initially "wet chemistry" analyzes but evolved to sophisticated techniques like X-Ray Fluorescence (XRF) or X-Ray Diffraction (XRD) analysis. Sub-sample collection, preparation and analysis typically present analysis results >1 hour later and the full results sometimes days after the elemental material passed the sample point. The use of a sub-sample weighing a few grams to represent 1000's of tons of mineral matter is one of the largest sources of analysis error.

Rapid analytical techniques that do not require sampling but analyze 100% of the material in situ or better yet in motion provide more timely minute by minute analytical information that gives the ability to optimize a mineral processing operation via sorting, batching or the blending of raw materials. The ability to know when sufficient elements of interest are present in the raw materials allows the mine operator or waste recycler to divert less economic matter from the process. This cuts the cost of extracting the useful elements and reduces the often hazardous waste products created during the mineral processing. To effectively detect useful elements requires the ability to see inside rocks, gravel and waste streams that often hide the useful elemental material. Some elements associated with bombs, explosives, drugs and other contraband can be hidden within normal materials and require detection through the concealment. This requires a sensor technology that will penetrate raw materials. The XRF and XRD techniques are typically surface or small sample techniques restricted to very small particle sizes. The on-line techniques of prompt Thermal or Fast neutron analysis with the detection of the signature elemental gamma rays can provide penetrations of order 30 cm to see into rocks and waste streams but unfortunately these techniques are not very discriminating and are typically restricted to detection limits greater than 0.01% for the more sensitive elements. A tabular example of the achievable sensitivities in simple material matrices (less than a dozen components) is given in Table 1. [R. J. Proctor, On-Line Prompt Gamma Neutron Activation Analyzers, Process/industrial Instruments and Controls Handbook, Fifth Edition, Gregory K. McMillan (ed), 10.161]

TABLE 1

Typical Belt Analyzer Elemental Sensitivity

| Sensitivity in Weight % [1] | Elements |
|---|---|
| <0.01% | Cl, Sc, Ti, Ni, Cd, Hg, Sm, Gd, Dy, Ho |
| 0.01-0.1% | S, V, Cr, Mn, Fe, Co, Cu, Rh, Ag, In, Hf, Ir, Au, Nd, Eu, Er, Yb, H |
| 0.1-0.3% | N, Na, Al, Si, K, Ca, Ga, Se, Y, Cs, La, W, Re, Os, Pt, Pr, Tm |
| 0.3-1.0% | Li, Be, Mg, P, Zn, As, Mo, Te, I, Ta, Pb, Ce, Tb, Lu, Th, U |
| 1.0-3.0% | C, Ge, Br, Sr, Zr, Ru, Pd, Sb, Tl |
| >3.0% | Other elements |

[1] Three-sigma detection limit in 10 minutes within an elementally simple rock matrix ≧150 mm thick.

In cases where weak elements are to be detected in a material matrix containing stronger more abundant elements or much greater than the a dozen components of a simple matrix the detection limits can easily be degraded by an order of magnitude worse than given in Table 1. As well as poor discrimination the neutron-gamma techniques are relative analysis methods where the elemental signals of interest must be normalized to correct for neutron flux variations in the samples due to matrix changes in moisture, density and neutron poison levels e.g. ppm levels of B, Li & Cd.

Analogous to the atomic resonant fluorescence process in atoms is the nuclear fluorescence process. The atomic process occurs with optical radiation in the electron-volt (eV) energy range but the nuclear process occurs with highly penetrating gamma ray radiation in the millions of electron-volts (MeV) range but unlike optical radiation most materials are mainly transparent to high energy gamma ray radiation. In the same way that atomic resonance is specific to one energy level of one atom the nuclear resonance is specific to one energy level of one nucleus. The technique of Gamma ray Resonance Absorption or Scattering makes use of this process to provide a very discriminating technique for elemental analysis. The main difficulty has always been to make the resonant X or Gamma Ray radiation.

The problem with making resonant X or Gamma ray radiation is that when a radioactive nucleus emits a gamma ray, the resultant gamma ray is no longer resonant with the original nuclear transition because of the Doppler energy loss caused by the recoil of the emitting nucleus. Also for a gamma ray to be absorbed it must possess energy large enough to excite a nuclear transition and provide energy for the resultant recoil of the scattering or absorbing nucleus. In some cases of nuclei in a crystalline solid the momentum is totally absorbed by the crystal and the gamma ray has its full energy. This is the Mössbauer Effect. Mössbauer isotopes are good sources of resonant gamma-rays but they only exist for specific elemental isotopes and they do not exist for gamma ray energies much above 0.1 MeV. This restricts Mössbauer sources to crystalline samples with special isotopes e.g. $^{57}$Fe, $^{192}$Ir. For typical unbound nuclei a resonant gamma ray must have the energy of the nuclear transition plus the energy lost to recoil during the emission and the energy required for absorption/scattering recoil. This energy difference δE from the gamma ray transition energy is given by $$\delta E = E^2/Mc^2 \text{[in } MeV\text{]}$$

Where E is the energy of the emitted photon in MeV, $Mc^2$ is the rest mass energy of the nucleus in MeV. This energy can be provided to the resonant gamma ray by emitting the gamma from a moving nucleus. The required Doppler shift velocity is given by $$V = c \cdot \delta E/E = c \cdot E/Mc^2 \text{[in m/sec]}$$

Where c is the speed of light in m/sec. The most efficient method of moving the radioactive nuclei is to physically move the radioactive source because then all emitting isotopes see the same corrective motion and the speed can be varied to allow non-resonant scattering background to be removed.

Titanium rotors have achieved tip speeds up to 1300 m/sec ["Resonance Fluorescence in Re187", H. Langhoff, Phys. Rev. Vol. 135, No. 1B, 1964]. A DOE ORNL group building composite flywheels for energy storage claims >1500 m/sec peripheral velocities with the limitation being manufacturing quality not the material strengths. Commercial flywheels for energy storage are advanced enough to use magnetic bearings and vacuum chambers and can achieve 1000 m/sec with 24 lb composite rotors and claimed lifetimes of greater than 10 years [Optimal Energy Systems, 2560 W. 237th Street, Torrance, Calif. 90505]. A 1000 m/sec velocity will energy correct an 0.6 MeV gamma ray by 2 eV or a 6 MeV gamma ray 20 eV.

An analysis of various methods for generating more generic resonant gamma rays for the borehole analysis of mineral matter is given by B. D. Sowerby, Nucl. Instr. and Meth. 108, 317 (1973). He concludes that an effective method is a gaseous radioactive source that emits a small fraction (1%) of its gamma rays from nuclei moving rapidly towards the scattering nuclei such that it compensates the Doppler shift. The problems are that the source must be strong and be able to be volatilized into a vapor. High temperature long lived radioactive vapors suitable for faster thermal nuclei are potentially environmentally dangerous and the technique has been tried but it has not been well accepted.

Another method of making resonant X or Gamma ray radiation uses a source of photons of distributed energies such that at least some of the photons possess the correct energy to be resonant with nuclei in the material sample to be analyzed. The application of Bremsstrahlung gamma ray radiation for this purpose is described by W. Bertozzi in U.S. Pat. Nos. 5,420,905 and 5,115,459. One problem is that the photon beam entering the sample material must be very intense to guarantee sufficient numbers of photons that actually satisfy resonance. This intensity is expensive to generate, requires exceptional safety precautions and makes a strong background of non resonant photons to the detriment of the analysis signal to noise. An advantage of this method is that many different elements in a sample material can be excited simultaneously but deconvolving the simultaneous scattered resonant photons from many elements in the presence of intense background radiation typically requires expensive detection systems.

SUMMARY OF THE INVENTION

This invention strives to overcome the limitation of poor-element discrimination in material analysis by using the technique of Gamma ray Resonance Scattering (GRS). This technique is very discriminating being sensitive only to the presence of the specifically chosen nuclei. GRS relies on a source of resonant gamma rays being either scattered or absorbed by the nuclei of interest. One problem in making a generic resonant gamma ray source is that a nuclear isotope must exist that produces a gamma ray resonant with the nuclei of interest. Such isotopes may not exist because they are non-radioactive or they may have short half lives (<1 month) that is a barrier to practical application. Even if the isotope exists it still must be capable of being either converted into a gaseous state or inserted into a mechanical rotor system for Doppler shift compensation.

According to one aspect of the present invention, instead of using a radioactive isotope implanted in a Doppler compensation system, a gamma ray source may be created from a stable target isotope using particle or photon irradiation dynamically in situ. One advantage of this is the ease of construction and general handling this allows as compared to an embedded radioactive source. Another advantage is that the gamma ray source can be from very short lived nuclear states allowing a much greater freedom in the choice of the analysis gamma ray transition. In the case of any short lived isotope it is noted that there will be a period of 3-4 half-lives before the gamma ray flux is at its peak after the first application of the particle or photon irradiation. Another advantage is that any intense irradiation of the target isotope by particles or photons can be well shielded with the resultant resonant gamma ray beam being allowed to exit the shield through collimating apertures. This beam will be of a much lower intensity than the primary exciting radiation. It will therefore be safer and easier to apply in practical systems.

For an excited platinum nucleus of mass $M=194$ $m_{proton}$ decaying with the emission of a gamma ray of energy $E=0.328448$ MeV the extra Doppler shift energy required is 0.5927 eV. To compensate this with source motion takes a velocity $V = c \cdot \delta E/E = 541$ m/sec which is achievable even with commercial long lived rotor technology.

It is known that prompt gamma-rays produced by neutron particle absorption in a target element are often energetically close enough to other element absorption lines to resonantly interact with them [B.Arad, G.Ben-David, Ann. Rev. Nucl. Sci. 24, 35 (1974)]. Resonant scattering from elements like Pb, Hg, Cd have been observed using the high fluxes of neutrons available in nuclear reactors. The second invention is to create these prompt gamma rays in a dynamic system either a rotor or gaseous absorber such that chance overlaps between prompt gamma ray lines and scattering element's energy levels can be fine tuned for optimum efficiency. The use of a ±1000 m/sec rotor allows fine tuning of 6 MeV gamma rays by ±20 eV. This allows resonant gamma-ray analysis at lower neutron fluxes suitable for elemental analysis in practical applications.

BRIEF DESCRIPTION OF THE DRAWINGS

The present invention will be better understood from the following detailed description of some exemplary embodiments of the invention, taken in conjunction with the accompanying drawings, in which like reference numerals refer to like parts, and in which.

DETAILED DESCRIPTION OF THE DRAWINGS

Figure 1:
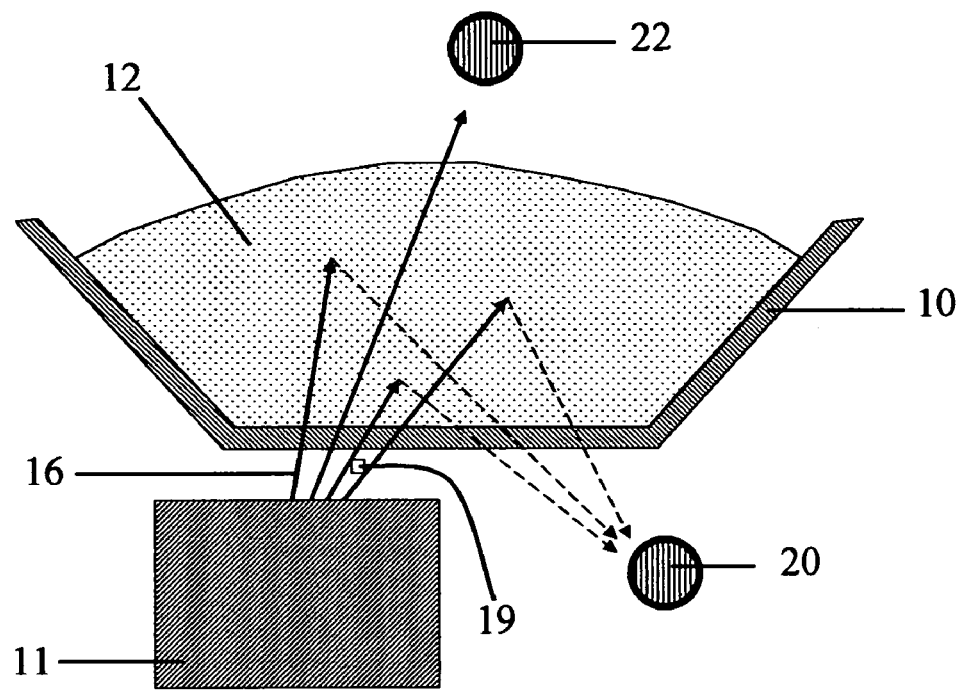
FIG. 1 is a cross sectional view of an analyzer apparatus according to a first embodiment of the invention.

FIGS. 1 to 4 illustrate an analyzer apparatus and a resonant gamma ray source for use in such an apparatus according to an exemplary embodiment of the present invention. The apparatus basically comprises a container 10 for a sample material to be analyzed 12 such as a mineral or other elemental matter, a resonant gamma ray source unit 11 positioned on one side of the container for directing resonant gamma rays (indicated by the arrows) into the sample material, a small flux monitor 19, a first detector 20 for detecting gamma rays resonantly scattered from a predetermined element or elements within the container in a first general direction (in this case a back scattering direction as indicated by the dotted outline arrow lines), and a second detector 22 positioned on the opposite side of the container from detector 20 for detecting transmitted and forward scattered gamma rays. The detectors are assumed to be energy sensitive so that they can discriminate against gamma rays that have lower or higher gamma ray energy than the resonant gamma rays. This is necessary for the best signal to noise. The small flux monitor detects the average gamma ray flux for long term drift correction.

The container 10 may be a conveyor belt for carrying a continuously moving mass of sample material to be analyzed continuously on-line, or may be a stationary container, a chute, a shipping container for scanning, or the like. In an exemplary embodiment, the resonant gamma rays emitted from source unit 11 illuminate the elemental sample material 12 carried on a conveyor belt 10 and the gamma rays 16 can be resonantly scattered below the belt into the industrially robust, large area, x-ray or gamma ray detector 20. Positioning of detector 20 to detect scattering at approximately 90 degrees gives the best signal to noise. The scattered signal is a measure of the number of resonant scattering nuclei and will change with belt loading changes in the elemental sample material until the loading exceeds a saturation bed depth. This bed depth is typically the e-folding penetration depth of the radiation in the elemental sample material. For example in coal this is 10 cm at 0.5 MeV. A belt load signal e.g. from a weigh scale, allows simple compensation for the elemental sample material loading changes on the scattered signals. The detector 22, similar to detector 20, looks at the transmitted and forward scattered radiation. The signals from detector 22 contain similar information on the number of resonant scattering nuclei but normally in a higher background of unscattered radiation. Again the signal must be combined with the knowledge of the belt loading from e.g. a weigh scale. With <1 MeV resonant gamma rays a very thick bed of sample material would strongly reduce the transmitted flux but embodiments that just detect the scattered resonant radiation do not require a transmission detector. For the best sensitivity mechanically refrigerated HPGe detectors can be used for 20 & 22. A stable, large area, CZT array detector or inexpensive Scintillator could also be used. The resonant gamma ray source is shielded with a radiation shield 18 to prevent resonant gamma rays directly exciting the scattered radiation detector 20.

Figure 2:
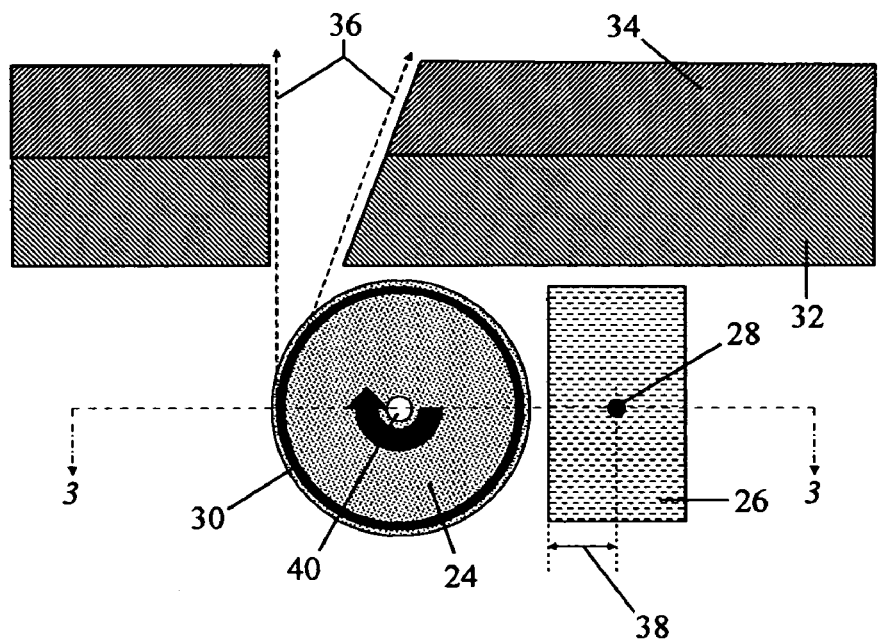
FIG. 2 is an enlarged cross-sectional view of a resonant gamma ray source unit for use in the apparatus of FIG. 1.
Figure 3:
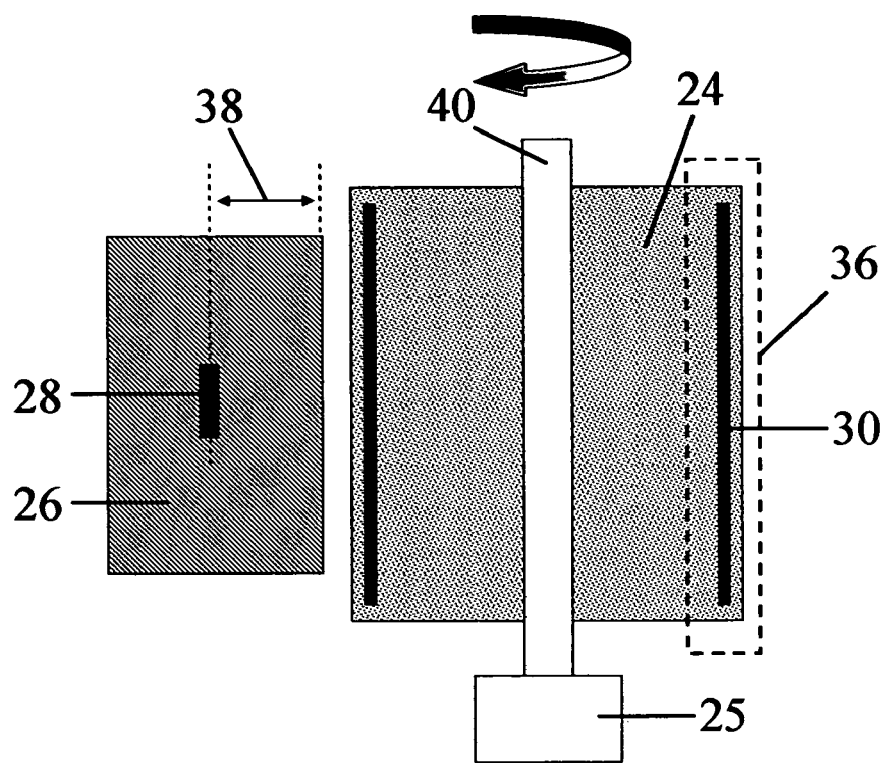
FIG. 3 is a sectional view on the lines 3-3 of FIG. 2, illustrating the housing aperture position relative to the rotor in dotted outline.
Figure 4:
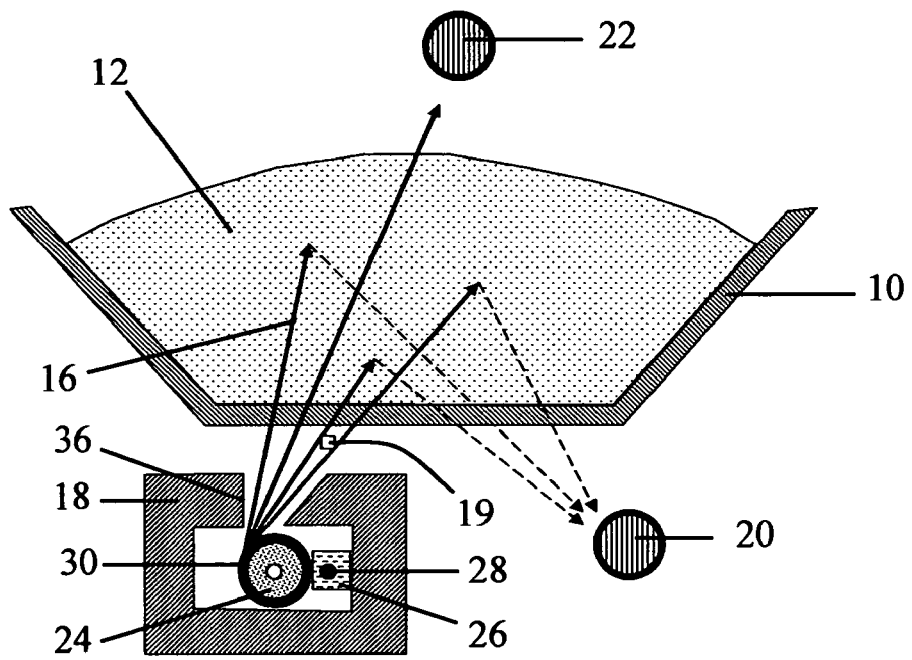
FIG. 4 is a cross sectional view of the apparatus similar to FIG. 1 illustrating the gamma ray source unit of FIGS. 2 and 3.

FIGS. 2 to 4 illustrate the resonant gamma ray source unit 11 in detail. Unit 11 basically comprises an outer housing 18 (see FIG. 4), a composite rotor 24 rotatably mounted in the housing with a central axle 40 rotated by rotor drive 25 at an adjustable speed, a cylindrical sleeve 30 embedded in the cylindrical rotor, the sleeve being of a selected target material or materials that are neutron activated by an adjacent neutron source 28. The sleeve may alternatively be attached on the outside of the rotor to surround the rotor. This is an advantage when the resonant gamma rays are of low energy and hence easily absorbed by any extra rotor material. When high energy, highly penetrating resonant gamma rays are being emitted then multiple sleeves of different materials may also be used of different radii such that when the rotor has a fixed angular velocity each sleeve has the correct velocity for its excited nuclei to emit resonant gamma rays. Each sleeve may also be a mixture of gamma ray generating materials whose gamma ray emissions can be brought into resonance by scanning the rotation rate of the rotor. The outer housing comprises a radiation shield having a first layer 32 of neutron reflecting and absorbing shield material and a second layer 34 of gamma ray shield material. The shield also provides radiation protection for nearby personnel and the detectors. It also acts to limit the portions of the sample material being analyzed. The housing has an aperture 36 which faces the container 10 and which is aligned with at least the tangential edge of the sleeve 30 in the rotor. The portion of the tangent seen from the sample material that has >95% of the appropriate velocity for resonance is approximately 10% of the circumference. In some cases of very low resonant gamma intensities where the system signal to noise is photon limited the aperture can be increased to expose a greater volume of sample material to resonant gamma rays. This would be relevant if normal operation is with a detected gamma signal to noise of less than 3 sigma in the required analysis time. In the illustrated embodiment, the neutron source material is in the form of a hollow cylinder, and the aperture 36 in this case comprises an elongate slot of length substantially equal to the length of the cylinder, and tangentially aligned on one side of the cylinder as best illustrated in FIG. 3. The embodiment shows a two detector system but for a large belt conveyor the resonant source assembly can be centered below (or above) the belt and detectors can be mounted to the left and right. In this case the aperture would be made more symmetric angling the same amount to the left and right.

The target element in the rotor is activated by typically thermal neutrons from the source 28 located on the side of the rotor 24 away from the beam defining aperture 36 in the neutron shield 32 and gamma ray shield 34. Thus in this embodiment mainly delayed activation products with lifetime greater than half the rotation time of the rotor about axle 40 can contribute gamma rays through the aperture. The prompt radiations (<$10^{-12}$ seconds) are mainly absorbed by the shields 32 and 34. An efficient shield is in at least two layers to allow it to be optimized to both reflect incident neutrons and absorb transmitted neutrons and gamma rays. In this embodiment layer 32 is a thick (>5 cm) hydrogenous material that both reflects and moderates incident fast neutrons in the first 2 cm but absorbs many neutrons that try to penetrate. In the second layer 34 gamma rays are absorbed with heavy metal materials like lead, bismuth or tungsten. A single combined neutron and gamma ray shield can be used but would be less effective. The neutron source can be either a radioisotope powered neutron source or a neutron generator. The neutron generator could be of the continuous or pulsed type. When using pulsed generators the resonant gamma rays can be measured whilst the generator is off. This eliminates the effects of shield and aperture leakage neutrons and improves the signal to noise ratio. A cost effective choice is the fission source $^{252}$Cf. In FIG. 3 is shown a plan view of an embodiment with a $^{252}$Cf neutron source 28 embedded in a moderator block 26. The choice of moderator materials and thickness 38 in front of the source is dependent on whether we want to maximize the thermal neutron flux at the active target material locations or optimize either the epithermal or fast flux. In this figure the thermal flux is being optimized especially as the rotor is made of a dense carbon fiber composite and hence is a good thermal moderator that helps boost the neutron flux in the side of the rotating cylinder closest to the neutron source. The moderator is then made of polyethylene with 0.5" thickness followed by 2" of graphite to achieve maximum thermal neutrons/cm$^2$/sec in the active target material 30. A moderator 26 doped with Boron nitride fibers or Cd or Li neutron poison dopants could be used for pure epithermal or fast neutron element activation analysis.

The variable speed drive 25 of rotor 24 allows the Doppler correction induced by the rotational velocity to be tailored for gamma ray resonance and also allows the comparison of the detected radiations when the gamma ray source 16 is and is not resonant. The photon energy of resonant or non-resonant gamma rays is almost identical such that systematics of gamma-ray transport and scattering through non resonant materials are virtually identical. This allows the unique determination of the signature of the elemental material of interest. This ability also allows the poor energy resolution of a Scintillator detector to still prove useful. The rotor may be of any combination of suitable low Z materials which are sufficiently strong, such as carbon, carbon composite, carbon fibers, nanotubes, composite plastic, plastic, silica, glass, ceramic, titanium, beryllium, aluminum, magnesium, etc.

FIG. 3 also shows a view of the active target elements 30 in the rotor 24. If the rotor only needs to run at low commercial ultracentrifuge speeds of ≦300 m/sec then it is not necessary to have a rotor in a vacuum enclosure and because the mechanical stresses are more reasonable and the rotor could have slots for removable target materials. FIG. 4 is a cross sectional view showing the use of rotor derived delayed, resonant gamma rays.

The choice of target materials is defined by the elements you wish to measure. Because short lived elements can be created from stable isotopes the choice can involve examples like $Z(n,n')^m Z$ reactions where the exact excited nuclide is created directly by exciting a nucleus with a fast neutron e.g. $^{197}$Au(n,n')$^{197m}$Au. The $^{197m}$Au then decays with a half life of 7.73 seconds to $^{197}$Au by emitting a 279 keV gamma ray. An $Z^A(n,\gamma)Z^{A+1}$ reaction is also a good choice where the $Z^{A+1}$ induced element decays with a short half live beta decay to the $(Z+1)^{A+1}$ or $(Z-1)^{A+1}$ nuclide of choice. e.g. $^{193}$Ir(n, γ)$^{194}$Ir where the $^{194}$Ir decays to $^{194}$Pt in 19.28 hours emitting a 328 keV gamma ray. This is an example where the system would require more than 2 days of flux stabilization before the maximum sensitivity was reached. Thus we could detect the 279 keV gold resonance with the $^{197}$Au(n,n')$^{197m}$Au reaction or the 328 keV platinum resonance with the beta decay of $^{194}$Ir made by $^{193}$Ir (n,γ)$^{194}$Ir.

It should be noted that if the mass of the target nuclides are very close e.g. $^{197}$Au & $^{194}$Pt and the emitted gamma rays have similar energies e.g. 279 & 328 keV then the resonance condition will be fulfilled at a similar velocity so that both target nuclides could be analyzed at the same time, provided the detector can resolve the 279 and 328 keV gamma rays.

Figure 5:
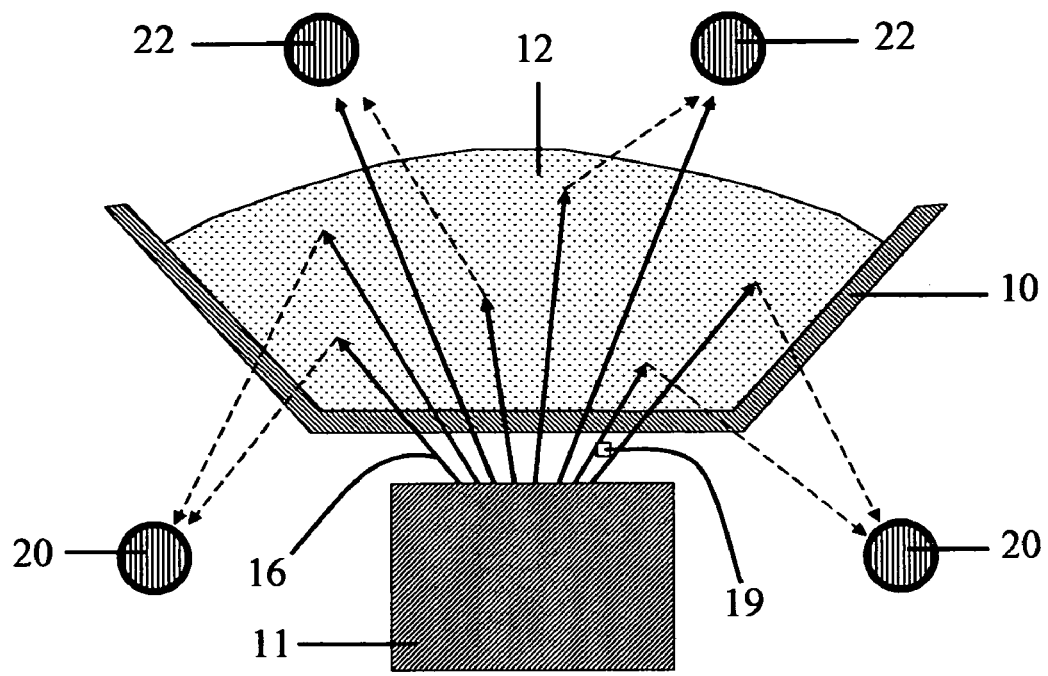
FIG. 5 is a cross sectional view of an analyzer apparatus according to a second embodiment of the invention.

FIG. 5 illustrates an analyzer apparatus and a resonant gamma ray source better suited for larger sized conveyor belts by adding further detectors. In this case, the resonant gamma ray source unit 11 is centrally located under the belt, with a larger aperture and two sets of detectors 20, 22, one set on each side of the unit 11.

Figure 6:
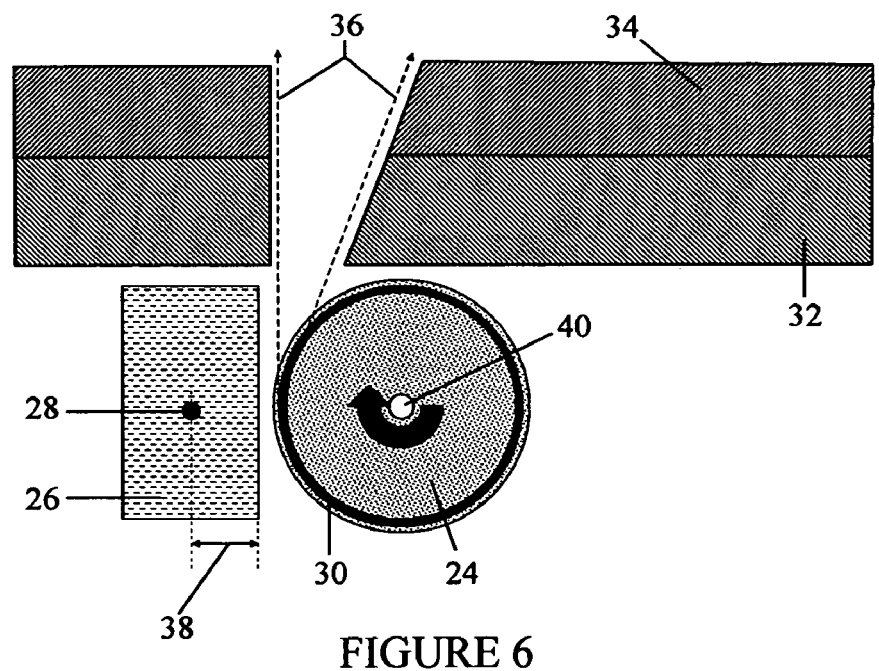
FIG. 6 is a cross sectional view of part of a modified gamma ray source unit according to another embodiment of the invention.
Figure 7:
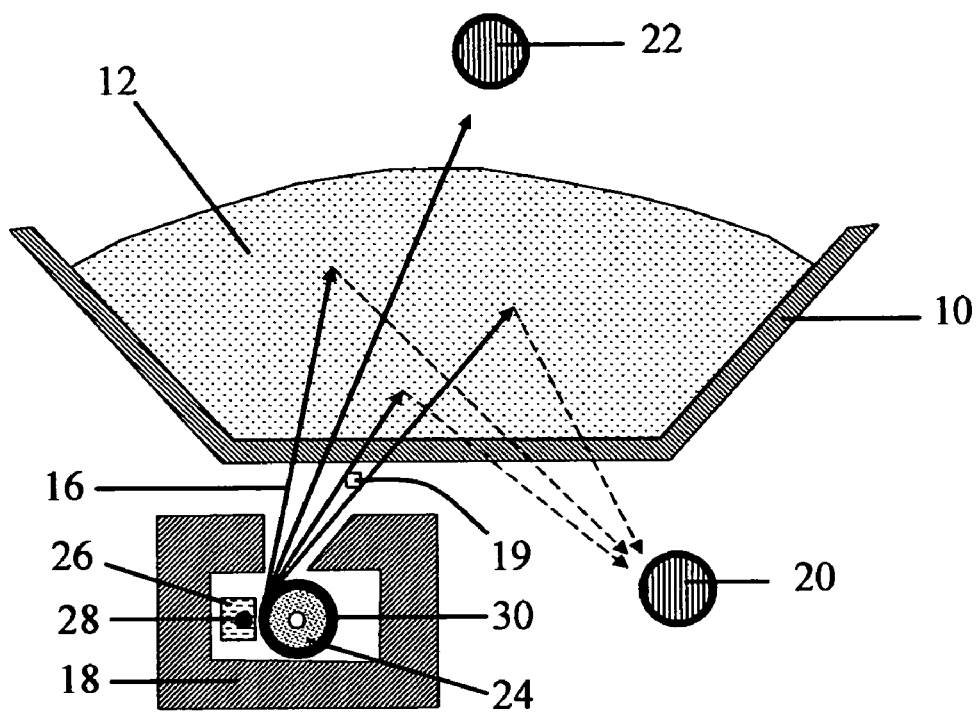
FIG. 7 is a cross sectional view of an analyzer apparatus according to another embodiment of the invention using the gamma ray source unit of FIG. 6.
Figure 8:
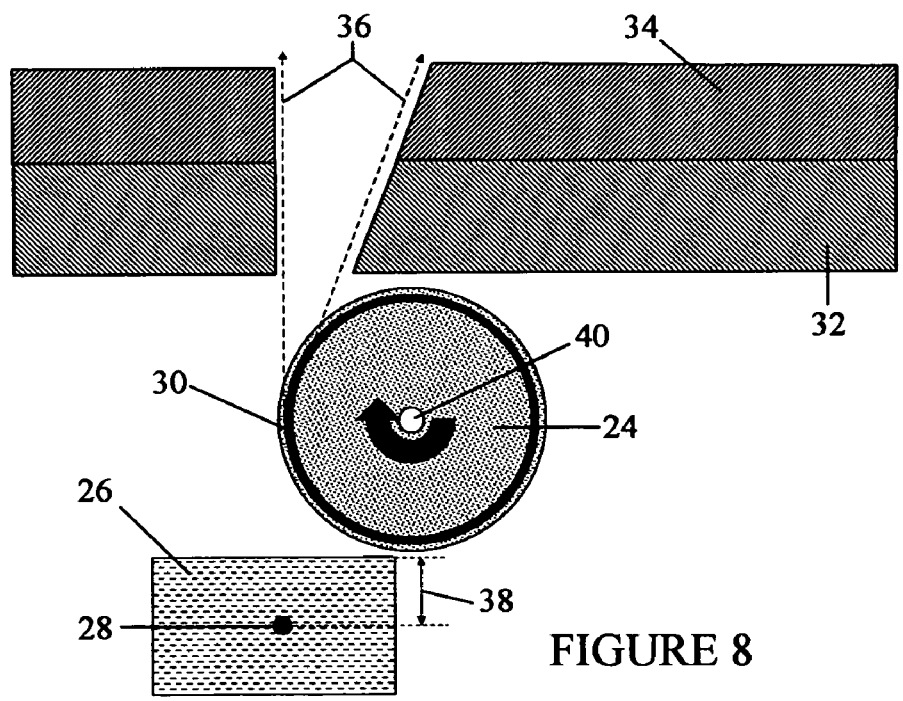
FIG. 8 is a cross sectional view of a modified gamma ray source unit having a different neutron source position.

FIG. 6 shows a modified resonant gamma ray source unit in which the neutron source 28 is located on the gamma ray aperture 36 side of the rotor. This further takes advantage of the $Z^A(n,\gamma)Z^{A+1}$ reaction but uses the prompt gamma rays produced as the $Z^{A+1}$ induced element decays to its ground states. The advantage of this is that prompt activation gamma rays from strong emitters like Z=Fe, Ti, Co, Cr, Cl, Ni can be used as 0-9 MeV resonant gamma ray beams to excite closely spaced lines in other elements like Pb, Hg, U, Pu, Ni, Cu. The use of the rotor allows fine tuning of the more penetrating 5-9 MeV gamma rays by ±20-30 eV to optimize known resonance conditions and also to generate new resonant conditions for new applications. FIG. 7 shows this applied to elemental material analysis. A limit to the method is that to compensate for larger energy changes the rotor is unable to rotate much faster than about 1500 m/sec because of fundamental limits to the strength of materials. One technique of providing larger energy compensation is to produce capture gamma rays directly from epithermal neutrons. If an element absorbs an epithermal neutron it recoils and typically emits a gamma-ray with a Doppler shifted energy. If the epithermal neutron source is emitting in the direction of rotor motion as shown in FIG. 8, then gamma resonance can be recovered and the rotor velocity changes can be used for fine tuning the resonance. This technique is unlikely to be as efficient as thermal neutron capture but it may allow better sensitivity for low Z elements. Shield layer 32 in this embodiment may incorporate hydrogenous materials like polyethylene or wax but doped with thermal neutron poisons like Boron, Lithium or Cadmium.

Figure 9:
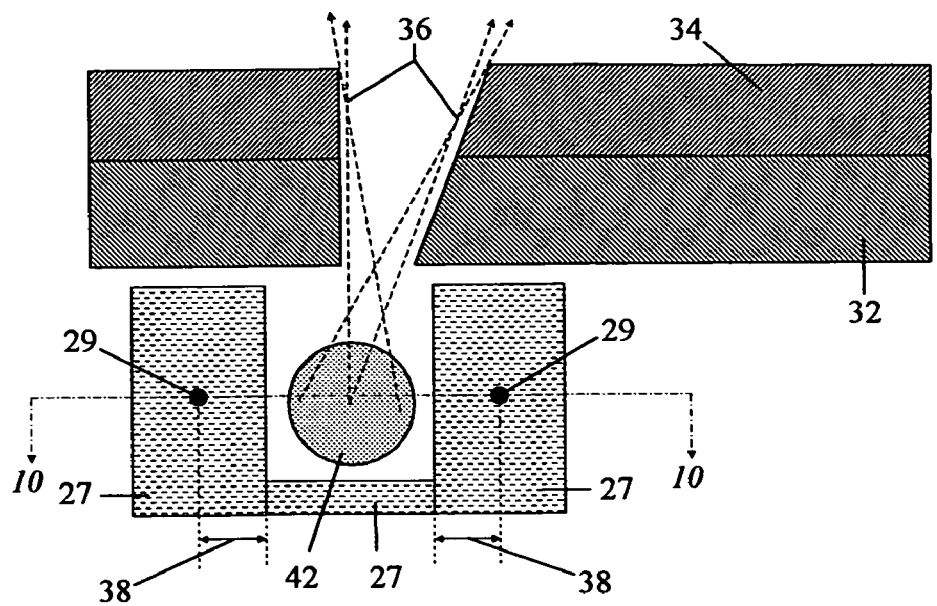
FIG. 9 is a cross sectional view of a modified gamma ray source unit using a gaseous source in place of the rotor.
Figure 10:
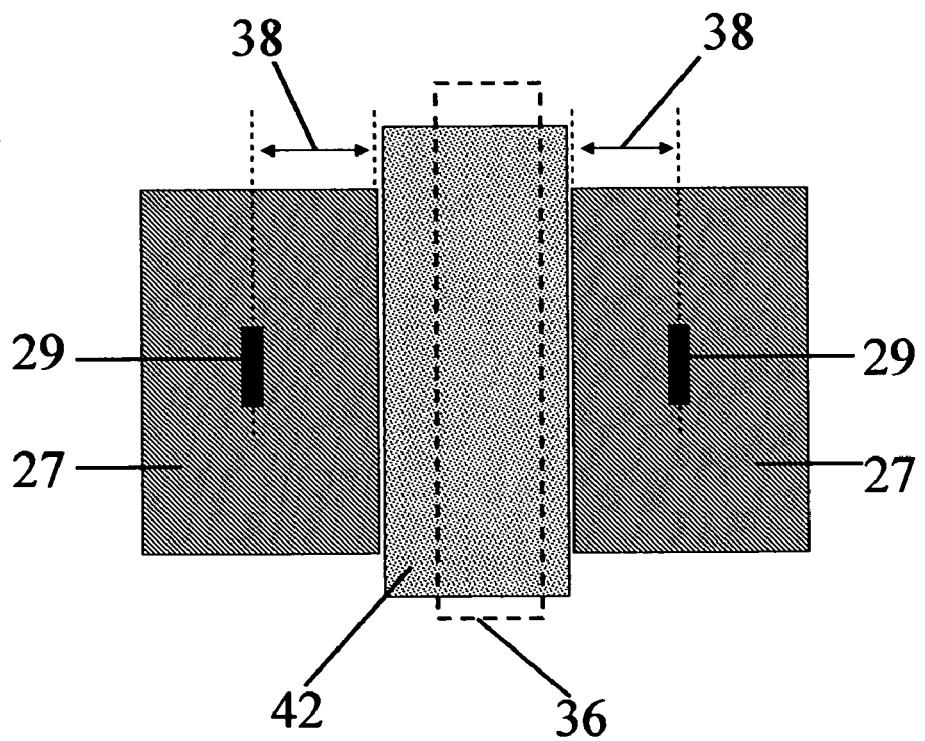
FIG. 10 is a cross section on the lines 10-10 of FIG. 9.
Figure 11:
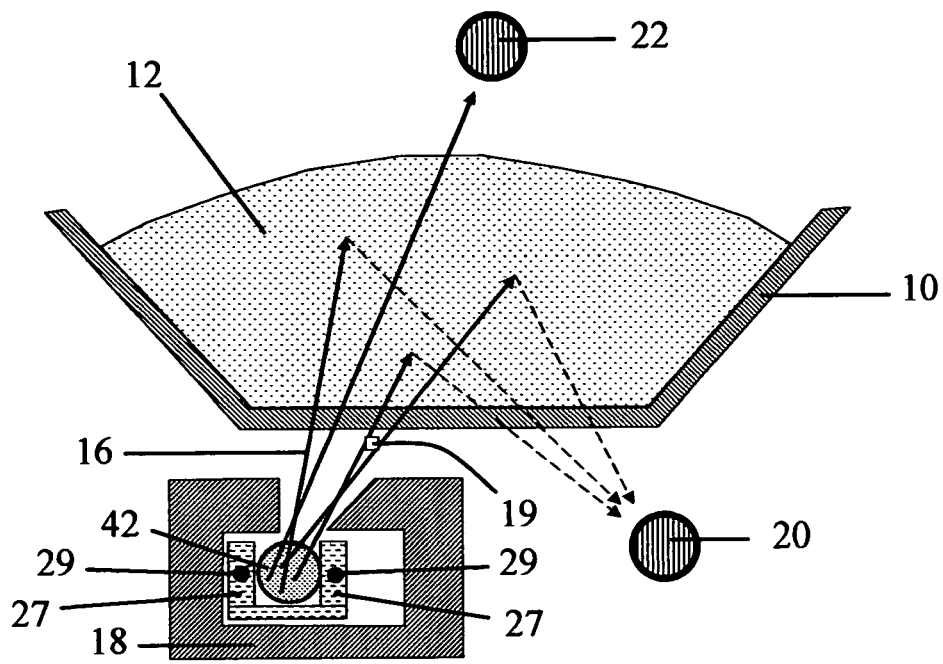
FIG. 11 is a cross sectional view of an analyzer apparatus using the gamma ray source unit of FIGS. 9 and 10.

Another method is both prompt gamma rays and/or delayed activation gamma rays from a gas or heated vapor 42 as shown in FIG. 9, with a cross section in FIG. 10 and demonstrated in FIG. 11. The Maxwellian thermal motion of the gaseous molecules acts to cause some of the gamma ray emitted isotopic gamma rays to be exactly compensated for the energy difference to achieve resonance. The use of a heating or cooling element allows the gas temperature to be changed to optimize the resonance efficiency. The velocities of many of the molecules when heated to 1000 degrees C. are considerably higher than the 1000 m/sec rotor velocities. This technique requires an approximately 100 times stronger radiation source than the rotor technique but can be applied to Hg vapor using the $^{199}$Hg(n,n')$^{199m}$Hg reaction to produce a gamma ray resonant with Hg or Nickel-64 Carbonyl a room temperature vapor using $^{64}$Ni(n, γ)$^{65}$Ni where the $^{65}$Ni decays to $^{65}$Cu in 2.65 hours emitting 1.481, 1.115 and 0.368 MeV gamma rays which are resonant with copper.

Figure 12:
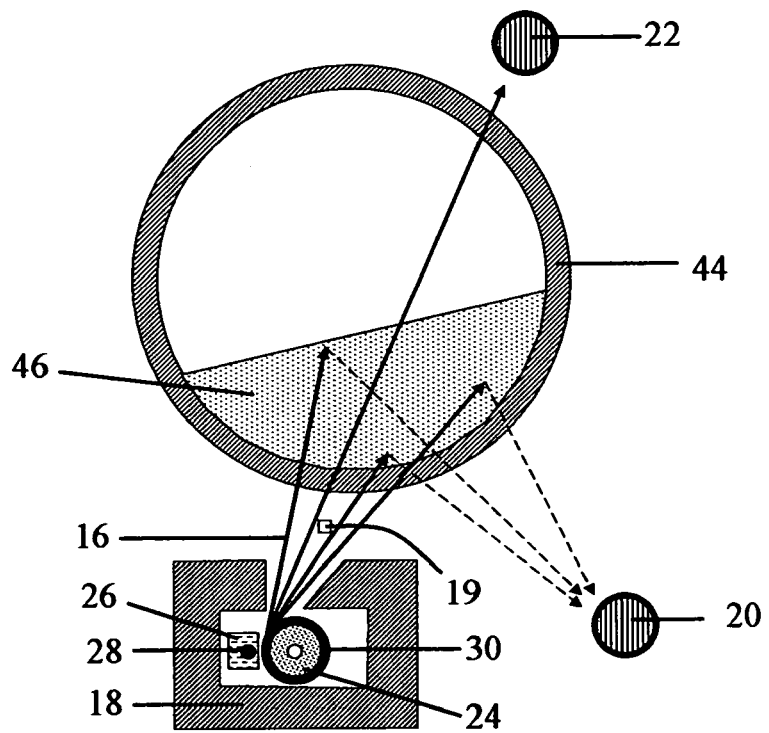
FIG. 12 is a cross sectional view of a modified analyzer apparatus for detecting temperature of specific elements of a sample material in a kiln.

The resonance width of emitted gamma rays is normally dominated by the Doppler motion of the nuclei which broadens the gamma ray lines to be almost 1 eV wide at room temperature. Thus another application could be the determination of the temperature of the nuclei of the target material by mapping the gamma ray resonance profile by varying the rotor speed. FIG. 12 shows this embodiment. A high energy gamma ray from prompt capture is necessary to penetrate the smelter/kiln wall and thermal insulation 44 to be scattered in the hot elemental material 46. Thus it may be possible to monitor the on-line temperature of an elemental species in a smelter/kiln independent of the structural component or gangue temperatures and with no adverse effects from corrosive environments. The temperature sensitivity of the mapping could be increased by reducing the width of the resonant lines by using a cold rotor to reduce the thermal broadening of the nuclei.

Figure 13:
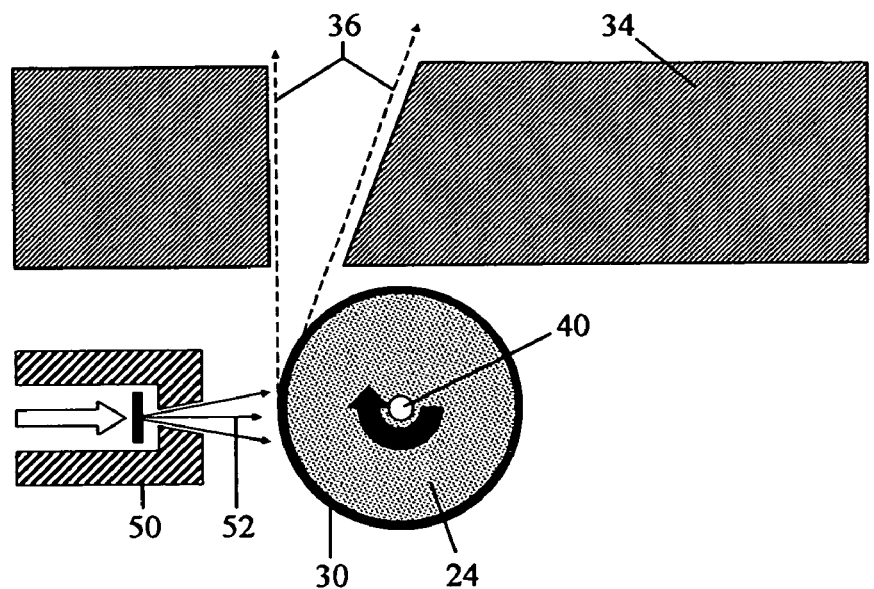
FIG. 13 is a cross sectional view of a modified gamma ray source unit using a charged particle or photon beam instead of a neutron source.
Figure 14:
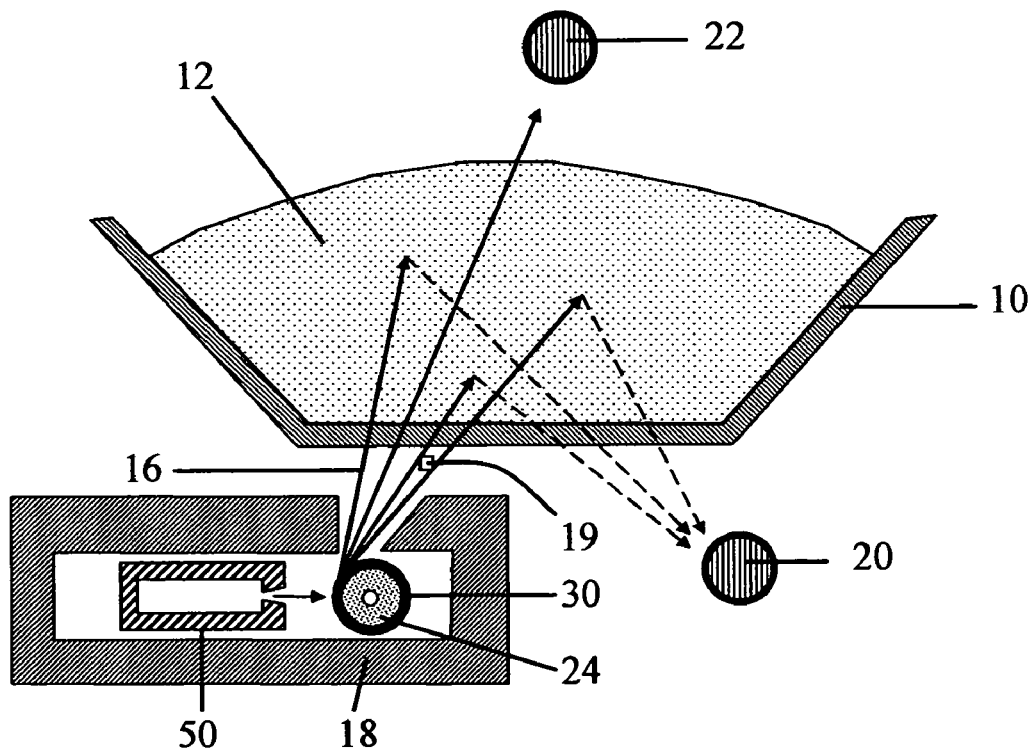
FIG. 14 is a cross sectional view of an analyzer apparatus using the gamma ray source unit of FIG. 13.
Figure 15:
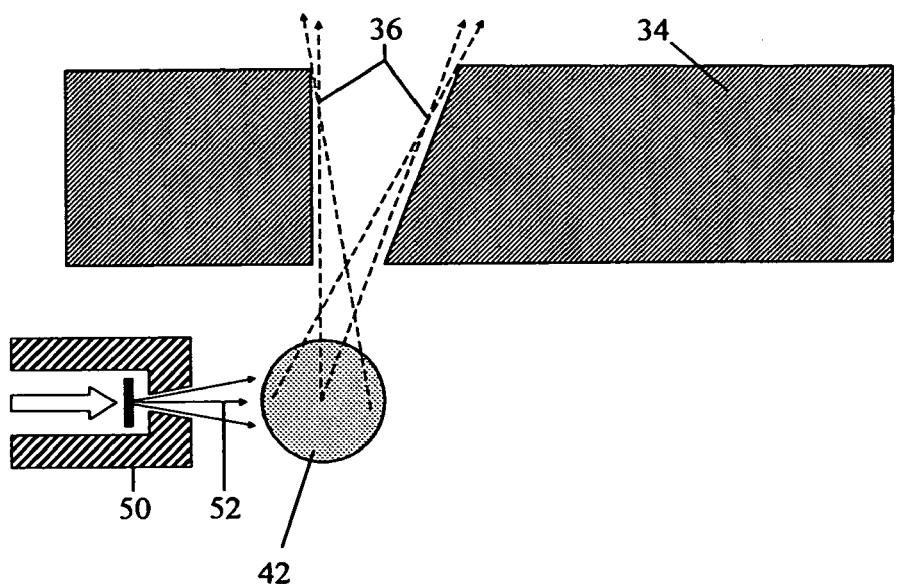
FIG. 15 is a cross sectional view of a modified gamma ray source unit using a gaseous source activated by a charged particle or photon beam.
Figure 16:
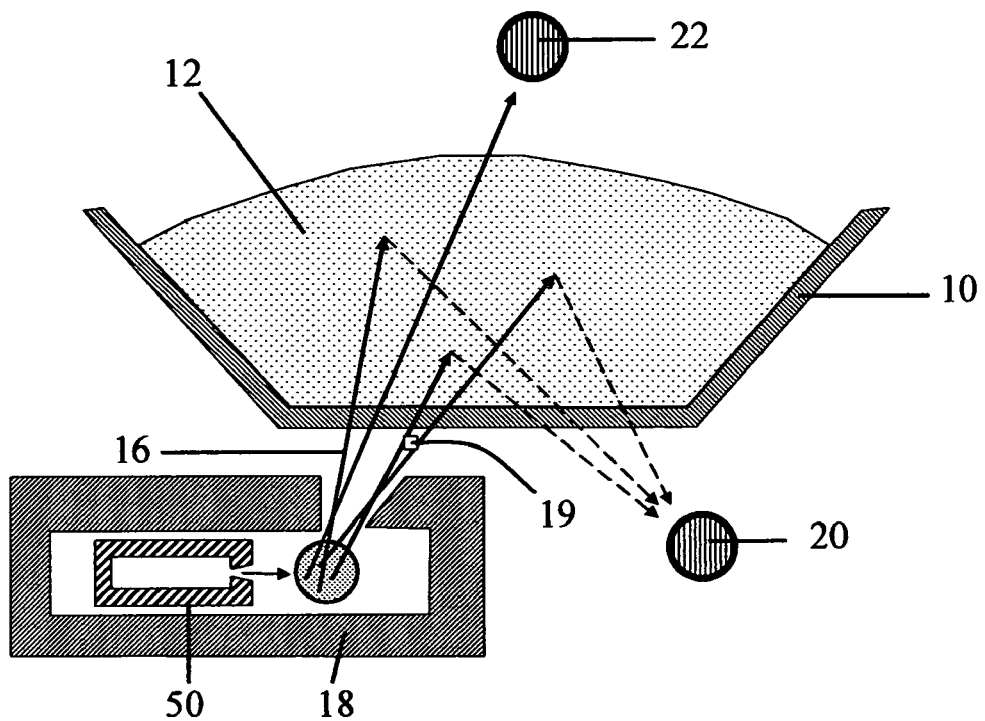
FIG. 16 is a cross sectional view of an analyzer apparatus using the gamma ray source unit of FIG. 15.

Another method of creating the gamma ray source directly from a stable isotope is using photon irradiation. Nuclear excitations and reactions can be induced when stable isotopes are bombarded by high energy photons. Irradiation by continuum radiation can create excited nuclear states via Z (γ, γ')Z* interactions that can promptly decay with the emission of Gamma rays or generate short lived metastable states Z (γ,γ')Z$^m$ like $^{197}$Au(γ, γ')$^{197m}$Au. The $^{197m}$Au then decays with a half life of 7.73 seconds to $^{197}$Au by emitting a 279 keV gamma ray. Photon irradiation can also induce particle emitting reactions like $Z^A$(γ, p)[Z−1]$^{A-1}$ or $Z^A$(γ, n)$Z^{A-1}$ which can generate prompt gamma rays from excited product nuclei and leave radioactive nuclei that may also decay with gamma ray emission. By selecting the target element/isotope to generate the desired gamma rays from the rotor or gaseous source, resonant gamma rays can be produced that can allow the analysis of an external material. Examples of appropriate photon sources can include isotopic gamma ray sources of energy for exciting isomeric states and >10 MeV linac electron accelerators to make high energy bremsstrahlung gamma rays for exciting many nuclear levels in the 0-10 MeV range. These penetrating photons can penetrate the wall of the rotor vacuum vessel or gaseous source container almost as well as neutrons. FIG. 13 shows a shielded source or accelerator 50 with a photon beam 52 exciting the target material 30 in rotor 24. FIG. 14 shows this applied to elemental material analysis. FIG. 15 shows a shielded source or accelerator 50 with a photon beam 52 exciting the gaseous target material 42. FIG. 16 shows this applied to elemental material analysis.

Another method of creating the gamma ray source directly from a stable isotope is using charged particle irradiation rather than neutron irradiation using the same apparatus as illustrated in FIGS. 13 and 15. Nuclear reactions and excitations are induced when stable isotopes are bombarded by particles like electrons, protons, deuterons, alpha particles (He nuclei) and higher mass nuclei. Reactions like $Z^A$(p, γ)[Z+1]$^{A+1}$ or $Z^A$(d, γ)[Z+1]$^{A+2}$ can generate prompt gamma rays and radioactive nuclei that can decay with gamma ray emission. By matching the target element/isotope to generate the correct gamma ray decaying nuclei to be made resonant with an external material we can analyze the external material. Any sequence of (p, n),(p, d), (p, alpha), etc reactions can also generate gamma emitting nuclei.

These irradiating particles are less penetrating than neutrons or high energy photons and so would typically be created in a vacuum common to the rotor and allowed to pass onto the rotor target surface 30. The advantage of the particle induced transformations is that intense beams can be formed to create many radioactive Gamma emitting nuclei. The disadvantage is that the target materials should be within a few microns of the surface of the rotor. One example is a fluorine containing compound or gas in a proton beam of greater than 230 KeV to give exited oxygen and an alpha particle from the F19 (p, α)O16 reaction. The oxygen decays with characteristic 6.129 & 7.2 MeV Gamma rays. FIG. 13 also shows a shielded source or accelerator 50 with a charged particle beam 52 exciting the target material 30 in rotor 24. FIG. 14 shows this applied to elemental material analysis. FIG. 15 also shows a shielded source or accelerator 50 with a particle beam 52 exciting the gaseous target material 42. FIG. 16 shows this applied to elemental material analysis.

Although some exemplary embodiments of the invention have been described above by the way of example only, it will be understood by those skilled in the field that modifications may be made to the disclosed embodiment without departing from the scope of the invention, which is defined by the appended claims.

The invention claimed is:

1. A material analyzer for identifying quantities of one or more elements in a material, comprising:
   a. a container for holding a sample material to be analyzed;
   b. a resonant gamma ray source unit for directing resonant gamma rays into the sample material in the container;
   c. at least one detector for detecting gamma rays resonantly scattered by at least one predetermined element in the sample material; and
   d. the resonant gamma ray source unit comprising:
      i. an outer housing having an inner chamber and an aperture directed towards the container;
      ii. the housing comprising gamma ray shield material and radiological shield material;
      iii. a moving gamma ray generator source of at least one target material mounted in the chamber, the target material being selected from a predetermined group of materials which emit resonant gamma rays when exposed to particles or photons, the source being directed towards said aperture; and
      iv. a source of particles or photons positioned in the chamber adjacent the gamma ray generator source.

2. The analyzer as claimed in claim 1, wherein the generator source has more than one target material for emitting different gamma rays to preferentially activate different elements in the sample material.

3. The analyzer as claimed in claim 1, wherein the moving gamma ray generator source comprises a rotor member and at least one gamma ray generator element associated with the rotor member.

4. The analyzer as claimed in claim 3, wherein the rotor is of a low Z material.

5. The analyzer as claimed in claim 4, wherein the rotor material is selected from the group consisting of: carbon, carbon composite, carbon fibers, nanotubes, composite plastic, plastic, silica, glass, ceramic, titanium, beryllium, aluminum and magnesium.

6. The analyzer as claimed in claim 3, wherein the rotor member is a solid cylinder of a first diameter having a central axis of rotation and the gamma ray generator element comprises a hollow cylinder.

7. The analyzer as claimed in claim 6, wherein the gamma ray generator cylinder is of smaller diameter than said first diameter and is embedded in said rotor.

8. The analyzer as claimed in claim 6, wherein said gamma ray generator cylinder is mounted over said rotor and is co-axial with said rotor axis.

9. The analyzer as claimed in claim 3, wherein the gamma ray generator element is of a predetermined material which emits resonant gamma rays on exposure to particles or photons.

10. The analyzer as claimed in claim 3, wherein the gamma ray generator element is of a predetermined material which decays to an element that emits resonant gamma rays on exposure to particles or photons.

11. The analyzer as claimed in claim 1, wherein the gamma ray generator comprises a target gas, temperature control means for controlling the temperature of the gas and an outer container holding the gas.

12. The analyzer as claimed in claim 11, wherein the gamma ray generator gas is of a predetermined material which emits resonant gamma rays on exposure to particles or photons.

13. The analyzer as claimed in claim 11, wherein the gamma ray generator gas is of a predetermined material which decays to an element that emits resonant gamma rays on exposure to particles or photons.

14. The analyzer as claimed in claim 1, wherein the moving gamma ray generator is elongate and the aperture comprises an elongate slot having a length substantially equal to the length of the gamma ray generator.

15. The analyzer as claimed in claim 1, including first and second detectors, the first detector being positioned to detect back scattered gamma rays and the second detector being positioned to detect forward scattered and transmitted gamma rays.

16. The analyzer as claimed in claim 1, wherein the gamma ray generator source is positioned on one side of the container, a first detector is positioned on the same side of the container as the gamma ray generator source for detecting back scattered gamma rays, and a second detector is positioned on the opposite side of the container to the gamma ray generator source.

17. The analyzer as claimed in claim 3, wherein the rotor member comprises a cylindrical rotor of a different material from the target material and the target material is embedded in said rotor.

18. The analyzer as claimed in claim 3, wherein more than one target material is embedded in said rotor.

19. The analyzer as claimed in claim 17, wherein the gamma ray generator source comprises an open ended cylindrical shell embedded in said cylindrical rotor and centered on said axis of rotation.

20. The analyzer as claimed in claim 19, wherein said cylindrical shell is of predetermined length and said aperture comprises a slot having a length substantially equal to the length of said shell, the slot being positioned such that a tangent to said shell passes through the slot.

21. The analyzer as claimed in claim 20, wherein the slot is offset to one side of the central axis of rotation.

22. The analyzer as claimed in claim 21, wherein the source of particles or photons is positioned on the opposite side of the rotor to the slot.

23. The analyzer as claimed in claim 22, wherein the source of particles or photons is positioned on the same side of the rotor to the slot.

24. The analyzer as claimed in claim 1, wherein the source of particles or photons is selected from the group consisting of a gamma ray photon source, and a charged particle source.

25. A method of detecting elements in a material, comprising the steps of:
containing a sample volume of material to be analyzed; placing a generator source on one side of the sample volume; the generator source being of at least one target material which emits resonant gamma rays when exposed to particles or photons; moving the gamma ray generator source; exposing the moving gamma ray generator source to a source of particles or photons whereby resonant gamma rays are emitted from the generator source; directing the resonant gamma rays into the sample volume; and detecting gamma rays resonantly scattered by at least one predetermined element in the material as a result of exposure to said resonant gamma rays, whereby the output of the detector can be used in analyzing characteristics of said predetermined element in said sample volume.

26. The method as claimed in claim 25, wherein the output of the detector is used to determine the amount of said predetermined element in said sample volume.

27. The method as claimed in claim 25, including the step of varying the speed of movement of said gamma ray generator source to produce a gamma ray resonance profile output from the detector, and calculating the temperature of the material in said sample volume based on the width of said gamma ray resonance profile.

28. The method as claimed in claim 25, wherein the step of moving the gamma ray generator source comprises embedding at least one target element in a rotor having a central axis of rotation, the source of particles or photons being positioned to one side of said axis of rotation, and rotating the rotor at a selected speed.

29. The method as claimed in claim 28, wherein the rotor speed is adjustable.

30. The method as claimed in claim 28, wherein a plurality of target elements are embedded in the rotor for emitting different gamma rays, whereby different elements in the sample volume are activated.

* * * * *